(12) United States Patent
Chun

(10) Patent No.: US 8,192,940 B2
(45) Date of Patent: Jun. 5, 2012

(54) METHOD FOR AMPLIFYING UNKNOWN DNA SEQUENCE ADJACENT TO KNOWN SEQUENCE

(75) Inventor: Jong Yoon Chun, Seoul (KR)

(73) Assignee: Seegene, Inc., Seoul (KR)

(*) Notice: Subject to any disclaimer, the term of this patent is extended or adjusted under 35 U.S.C. 154(b) by 593 days.

(21) Appl. No.: 12/226,749

(22) PCT Filed: May 4, 2006

(86) PCT No.: PCT/KR2006/001694
§ 371 (c)(1),
(2), (4) Date: Oct. 27, 2008

(87) PCT Pub. No.: WO2007/129778
PCT Pub. Date: Nov. 15, 2007

(65) Prior Publication Data
US 2009/0298128 A1      Dec. 3, 2009

(51) Int. Cl.
*C12Q 1/68*  (2006.01)
*C12P 19/34* (2006.01)
*C07H 21/04* (2006.01)

(52) U.S. Cl. .......... 435/6.12; 435/91.2; 536/24.33

(58) Field of Classification Search .......... None
See application file for complete search history.

(56) References Cited

U.S. PATENT DOCUMENTS
5,998,170 A * 12/1999 Arakawa et al. ............. 435/69.4
2002/0155448 A1 * 10/2002 Cai et al. ..................... 435/6

FOREIGN PATENT DOCUMENTS
WO    WO 03/050305 A1    6/2003
WO    WO 2005/045073 A1    5/2005
WO    WO 2005/083120 A1    9/2005

OTHER PUBLICATIONS
Watanabe et al. Design and evaluation of PCR primers to amplify bacterial 16S ribosomal DNA fragments used for community fingerprinting. Journal of Microbiological Methods (2001) 44: 253-262.*
DNA Walking SpeedUp™ Premix Kit User Manual (Sep. 2004), 24 pages.*
Kobayashi et al. Nucleic Acids Symposium Series (2004) 48: 225-226.*
Kim, et al., "Annealing Control Primer System for Identification of Differentially Expressed Genes on Agarose Gels", In: Biotechniques, Mar. 2004, vol. 36(3), pp. 424-435—see whole document.
International Search Report for corresponding international application PCT/KR2006/001694—date of mailing: Jan. 29, 2007.

* cited by examiner

*Primary Examiner* — Angela M Bertagna
(74) *Attorney, Agent, or Firm* — Gianna Julian-Arnold; Saul Ewing LLP

(57) ABSTRACT

The present invention relates to a method for amplifying an unknown nucleotide sequence adjacent to a known nucleotide sequence, which comprises the step of performing an amplification of the unknown nucleotide sequence using a DNA walking annealing control primer (DW-ACP) and a target specific primer (TSP) hybridizable with a site on the known nucleotide sequence.

25 Claims, 4 Drawing Sheets

M, 100 bp DNA ladder
A, DW-ACP-A
T, DW-ACP-T
G, DW-ACP-G
C, DW-ACP-C

Fig. 3

Identification of MFG insertion sites by human blat search

| Clone | Chromosome | STRAND | Start | End* (insertion site) |
|---|---|---|---|---|
| DW1 | 1 | + | 9843694 | 9844037 |
| DW2 | 13 | + | 40059031 | 40059568 |
| DW3 | 16 | + | 68156026 | 68156201 |
| DW4 | 2 | + | 25429017 | 25429108 |
| DW5 | 2 | + | 25429022 | 25429108 |
| DW6 | 21 | - | 41407558 | 41408014 |
| DW7 | 19 | - | 12884434 | 12884823 |
| DW8 | 7 | - | 68695357 | 68696030 |
| DW9 | 16 | - | 73665022 | 73665507 |
| DW10 | 7 | + | 867386 | 867600 |
| DW11 | 4 | - | 90007703 | 90008006 |
| DW12 | 16 | - | 30455287 | 30455486 |

SEQUENCE LISTING

```
<160> NUMBER OF SEQ ID NOS: 11

<210> SEQ ID NO 1
<211> LENGTH: 33
<212> TYPE: DNA
<213> ORGANISM: Artificial Sequence
<220> FEATURE:
<223> OTHER INFORMATION: DW-ACP1-A (Synthetic Construct)
<220> FEATURE:
<221> NAME/KEY: misc_feature
<222> LOCATION: (22)..(28)
<223> OTHER INFORMATION: n denotes deoxyinosine

<400> SEQUENCE: 1
tcacagaagt atgccaagcg annnnnnnac acg                               33

<210> SEQ ID NO 2
<211> LENGTH: 33
<212> TYPE: DNA
<213> ORGANISM: Artificial Sequence
<220> FEATURE:
<223> OTHER INFORMATION: DW-ACP1-C (Synthetic Construct)
<220> FEATURE:
<221> NAME/KEY: misc_feature
<222> LOCATION: (22)..(28)
<223> OTHER INFORMATION: n denotes deoxyinosine

<400> SEQUENCE: 2
tcacagaagt atgccaagcg annnnnnncc acg                               33

<210> SEQ ID NO 3
<211> LENGTH: 33
<212> TYPE: DNA
<213> ORGANISM: Artificial Sequence
<220> FEATURE:
<223> OTHER INFORMATION: DW-ACP1-T (Synthetic Construct)
<220> FEATURE:
<221> NAME/KEY: misc_feature
<222> LOCATION: (22)..(28)
<223> OTHER INFORMATION: n denotes deoxyinosine

<400> SEQUENCE: 3
tcacagaagt atgccaagcg annnnnnntc acg                               33

<210> SEQ ID NO 4
<211> LENGTH: 33
<212> TYPE: DNA
<213> ORGANISM: Artificial Sequence
<220> FEATURE:
<223> OTHER INFORMATION: DW-ACP1-G (Synthetic Construct)
<220> FEATURE:
<221> NAME/KEY: misc_feature
```

```
<222> LOCATION: (22)..(28)
<223> OTHER INFORMATION: n denotes deoxyinosine

<400> SEQUENCE: 4
tcacagaagt atgccaagcg annnnnnngc acg                                    33

<210> SEQ ID NO 5
<211> LENGTH: 33
<212> TYPE: DNA
<213> ORGANISM: Artificial Sequence
<220> FEATURE:
<223> OTHER INFORMATION: DW-ACP2-N (Synthetic Construct)
<220> FEATURE:
<221> NAME/KEY: misc_feature
<222> LOCATION: (26)..(29)
<223> OTHER INFORMATION: n denotes deoxyinosine

<400> SEQUENCE: 5
tcacagaagt atgccaagcg aggggnnnnc acg                                    33

<210> SEQ ID NO 6
<211> LENGTH: 21
<212> TYPE: DNA
<213> ORGANISM: Artificial Sequence
<220> FEATURE:
<223> OTHER INFORMATION: Universal primer (Synthetic Construct)

<400> SEQUENCE: 6
tcacagaagt atgccaagcg a                                                 21

<210> SEQ ID NO 7
<211> LENGTH: 30
<212> TYPE: DNA
<213> ORGANISM: Artificial Sequence
<220> FEATURE:
<223> OTHER INFORMATION: MFG-TSP1 (Synthetic Construct)

<400> SEQUENCE: 7
cgaagtccct gggacgtctc ccagggttgc                                        30

<210> SEQ ID NO 8
<211> LENGTH: 36
<212> TYPE: DNA
<213> ORGANISM: Artificial Sequence
<220> FEATURE:
<223> OTHER INFORMATION: MFG-TSP2 (Synthetic Construct)

<400> SEQUENCE: 8
gtcagttcca ccacgggtcc gccagataca gagcta                                 36

<210> SEQ ID NO 9
<211> LENGTH: 22
<212> TYPE: DNA
<213> ORGANISM: Artificial Sequence
<220> FEATURE:
<223> OTHER INFORMATION: MFG-TSP3 (Synthetic Construct)

<400> SEQUENCE: 9
ataaggcaca gggtcatttc ag                                                22

<210> SEQ ID NO 10
<211> LENGTH: 30
<212> TYPE: DNA
<213> ORGANISM: Artificial Sequence
<220> FEATURE:
<223> OTHER INFORMATION: MFG-DSO-TSP1 (Synthetic Construct)
<220> FEATURE:
<221> NAME/KEY: misc_feature
```

```
<222> LOCATION: (17)..(21)
<223> OTHER INFORMATION: n denotes deoxyinosine

<400> SEQUENCE: 10
cgaagtccct gggacgnnnn ncagggttgc                                   30

<210> SEQ ID NO 11
<211> LENGTH: 36
<212> TYPE: DNA
<213> ORGANISM: Artificial Sequence
<220> FEATURE:
<223> OTHER INFORMATION: MFG-DSO-TSP2 (Synthetic Construct)
<220> FEATURE:
<221> NAME/KEY: misc_feature
<222> LOCATION: (21)..(25)
<223> OTHER INFORMATION: n denotes deoxyinosine

<400> SEQUENCE: 11
gtcagttcca ccacgggtcc nnnnnataca gagcta                            36
```

METHOD FOR AMPLIFYING UNKNOWN DNA SEQUENCE ADJACENT TO KNOWN SEQUENCE

BACKGROUND OF THE INVENTION

1. Field of the Invention

The present invention relates to a method for amplifying an unknown nucleotide sequence adjacent to a known nucleotide sequence, in particular to a method for amplifying an unknown nucleotide sequence using uniquely designed primers and its applications.

2. Description of the Related Art

The polymerase chain reaction (PCR) presents the most effective method for selectively amplifying specific DNA fragments. In the PCR procedure, oligonucloetides complementary to the known 5' and 3' sequences flanking the target nucleic acid serve as "primers" and play a key role.

Application of PCR to isolate and analyze a particular DNA region requires knowledge of the DNA sequences flanking the region of interest. This generally limits amplification to regions of known DNA sequence. In the absence of the necessary sequence information, PCR amplification of a target DNA fraction in a complex DNA population is likely to result in the amplification of non-target DNA.

Many PCR-based methods have been developed and modified to isolate an unknown DNA sequence that flanks regions of known sequences. They include, inverse PCR (Triglia et al., 1988), panhandle PCR (Shyamala et al., 1989; Jones and Winistorfer, 1997), vectorette PCR (Arnold et al., 1991), anchored PCR (Roux et al., 1990), AP-PCR (Dominguez et al., 1994; Trueba and Johnson, 1996), capture PCR (Lagerstrom et al., 1991), and adapter- or cassette-ligated PCR (Iwahana et al., 1994; Riley et al., 1990; Siebert et al., 1995; Willems, 1998; Kilstrup and Kristiansen, 2000).

However, these methods have limitations such as the need to digest the DNA with restriction enzymes, ligate the digested DNA with linkers or with double-stranded, partially double-stranded, or single-stranded oligonucleotide cassettes, and purify and/or subclone the products before sequencing. The need for multiple steps in these protocols makes them cumbersome and inefficient. Furthermore, in these methods, the common problem is high background and non-specific products due to non-specific binding of the vector, adaptor, cassette, or tail primers.

Therefore, the methodology was further improved to provide a biotin/streptavidin system to capture biotinylated fragments of interest before the nested PCR is carried out (Rosenthal and Jones, 1990; Mishra et al. 2002). This method show an improvement to reduce the noise and to allow the amplification of the flanking region of any known sequence but requires a complicated procedure of immobilized step and also a lot of cost.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

To be free from the shortcomings of the conventional technologies described above, the present inventor has intensively researched to develop approaches capable of fundamentally and completely removing the high background problems in the amplification of unknown sequence, and as a result found a novel method for amplifying an unknown sequence adjacent to a known sequence, which permits to amplify an unknown sequence in a much more reliable and convenient manner.

Accordingly, it is an object of this invention to provide a method for amplifying an unknown nucleotide sequence adjacent to a known nucleotide sequence.

It is another object of this invention to provide a target specific primer for amplifying an unknown nucleotide sequence.

It is still another object of this invention to provide a kit for amplifying an unknown nucleotide sequence.

Other objects and advantages of the present invention will become apparent from the detailed description to follow taken in conjugation with the appended claims and drawings.

BRIEF DESCRIPTION OF THE DRAWINGS

FIG. 3 represents the results of the identification of MFG insertion sites into human genome sequences. The cloned PCR products are named as DW#.

DETAILED DESCRIPTION OF THIS INVENTION

Figure 1A:
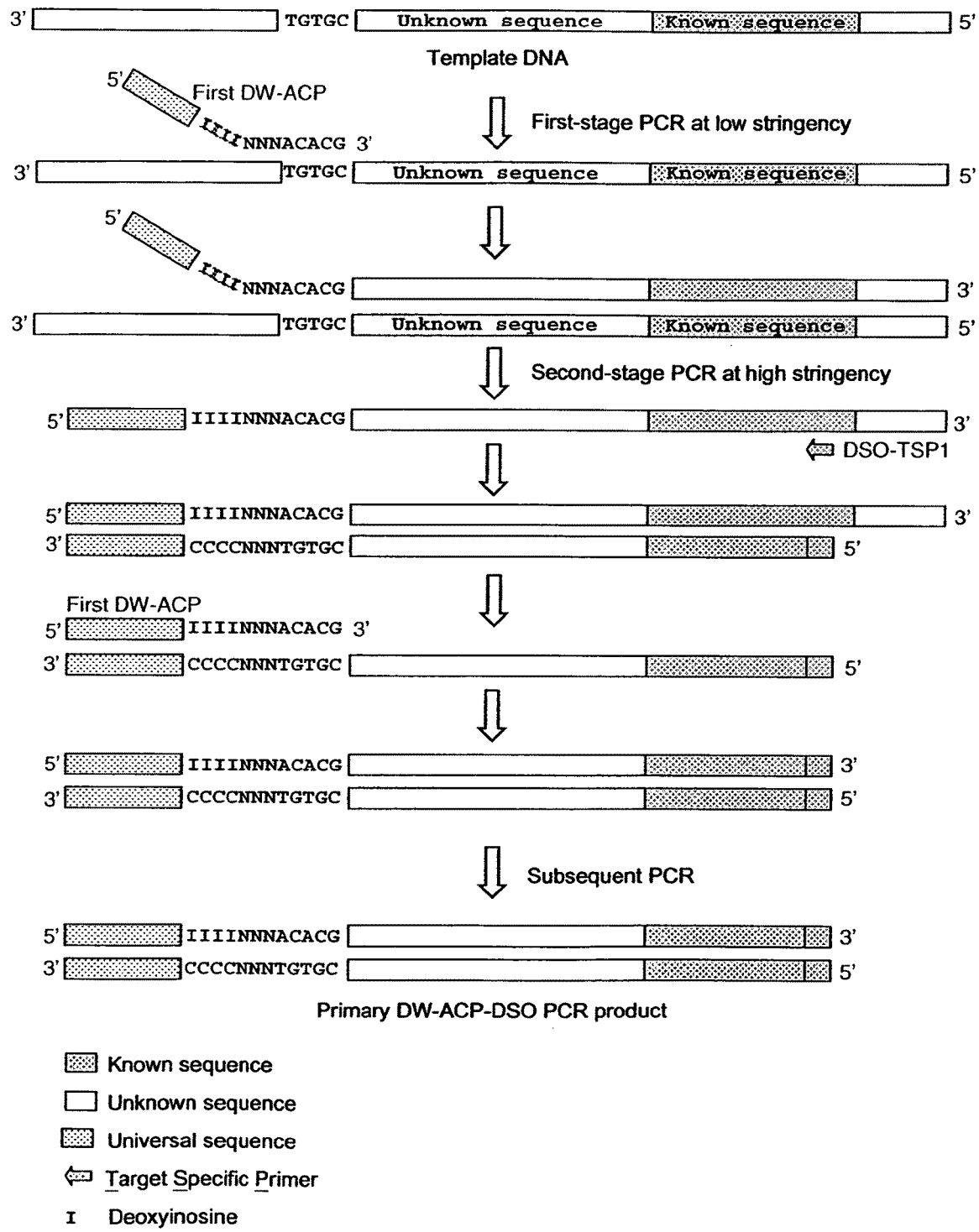
FIG. 1A shows a schematic representation of one specific embodiment of the primary amplification process using a first degenerate DNA walking annealing control primer (DW-ACP) (SEQ ID NO:1) and a first target-specific primer having a dual specificity oligonucleotide structure (DSO-TSP1) (SEQ ID NO:10).
Figure 1B:
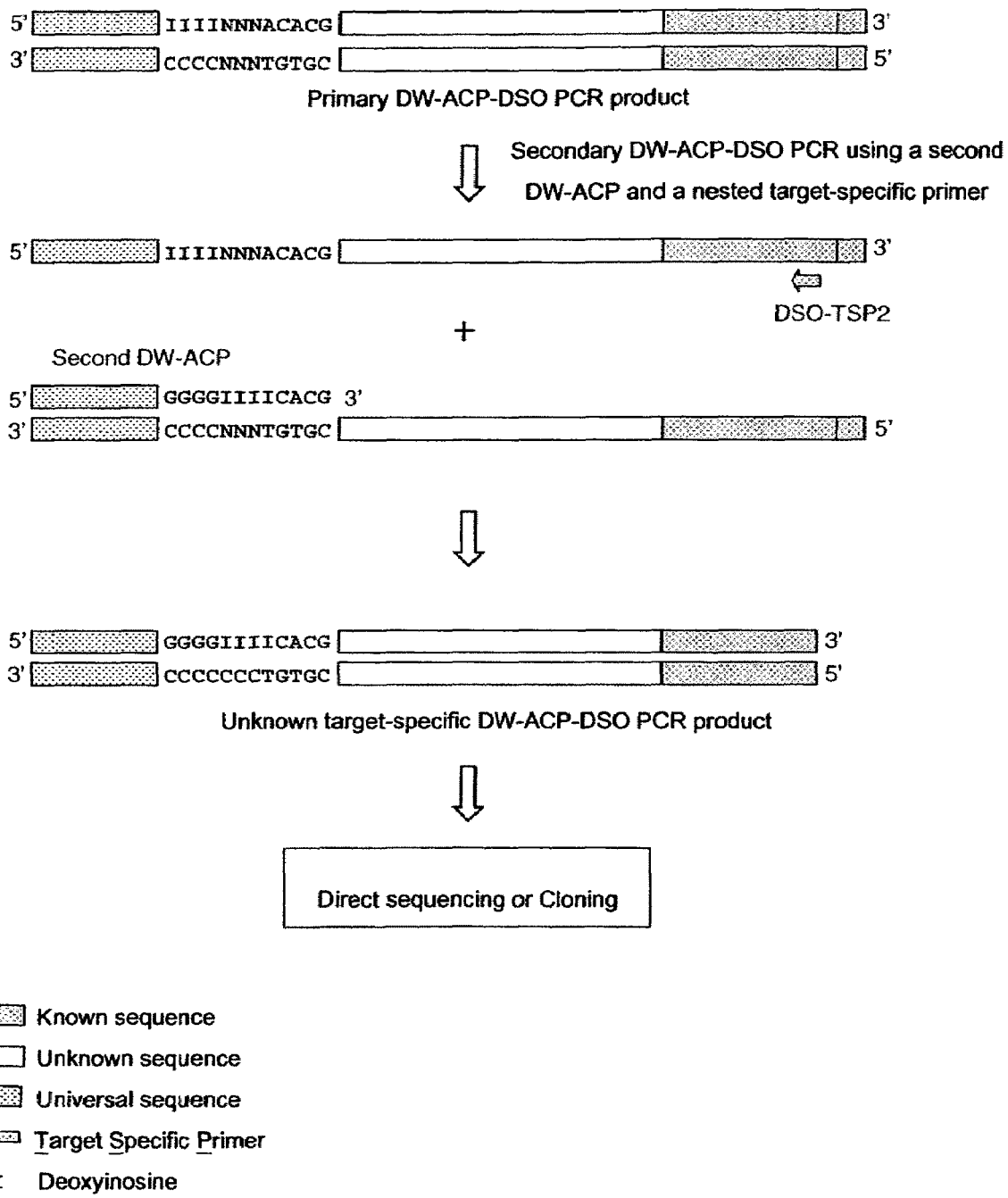
FIG. 1B schematically represents one specific embodiment of the secondary amplification process using a second DW-ACP (SEQ ID NO:5) and a second target-specific primer having a dual specificity oligonucleotide structure (DSO-TSP2) (SEQ ID NO:11).

In one aspect of this invention, there is provided a method for amplifying an unknown nucleotide sequence adjacent to a known nucleotide sequence, which comprises the step of (a) performing a primary amplification of the unknown nucleotide sequence using a DNA walking annealing control primer (DW-ACP) and a first target specific primer (TSP) hybridizable with a site on the known nucleotide sequence; in which the step (a) comprises: (a-1) performing a first-stage amplification of the unknown nucleotide sequence at a first annealing temperature, comprising at least one cycle of primer annealing, primer extending and denaturing, using a first degenerate DW-ACP containing (i) a degenerate random nucleotide sequence to hybridize with the unknown nucleotide sequence and (ii) a hybridizing nucleotide sequence substantially complementary to a site on the unknown nucleotide sequence, wherein the first annealing temperature enables the first degenerate DW-ACP to function as a primer, whereby a first degenerate DW-ACP extension product is generated; and (a-2) performing a second-stage amplification of the amplification product generated from step (a-1) at a second annealing temperature which is higher than the first annealing temperature, comprising at least one cycle of primer annealing, primer extending and denaturing using the first degenerate DW-ACP as used in the step (a-1) and the TSP, under conditions in which each primer anneals the its target nucleotide sequence, whereby a primary amplification product is generated.

The subject invention pertains to a unique method for selectively amplifying an unknown DNA sequence adjacent to regions of known sequences from a DNA or a mixture of nucleic acids using a DNA walking annealing control primer (hereinafter referred to as "DW-ACP") and a novel target specific primer.

To overcome the problems of the current DNA (or genome) walking methods including multiple and complicated steps and the inherent background of PCR-based methods, the Annealing Control Primer (ACP) system, which has been developed by the present inventor and disclosed in WO 03/050305, is modified to selectively amplify an unknown sequence adjacent to regions of known sequences. Since the ACP system is capable of dramatically improving amplification specificity, the use of ACP fundamentally prevents the non-specific priming of a primer during amplification and also simplifies the amplification process in this application.

According to a preferred embodiment, the first degenerate DW-ACP has a general formula I:

$$5'\text{-}X_p\text{-}Y_q\text{-}Z_r\text{-}Q_s\text{-}3' \qquad (I)$$

wherein, $X_p$ represents a 5'-end portion having a pre-selected nucleotide sequence, $Y_q$ represents a regulator portion comprising at least two universal base or non-discriminatory base analog residues, $Z_r$ represents a degenerate random sequence portion having a degenerated random nucleotide sequence, $Q_s$ represents a 3'-end portion having a hybridizing nucleotide sequence substantially complementary to a site on said unknown nucleotide sequence to hybridize therewith, p, q, r and s represent the number of nucleotides, and X, Y, Z and Q are deoxyribonucleotide or ribonucleotide.

The first degenerate DW-ACP of this invention has been developed for the amplification of an unknown nucleotide sequence adjacent to a known nucleotide sequence using and modifying the principles of annealing control primers developed by the present inventor and disclosed in WO 03/050305, the teachings of which are incorporated herein by reference in their entity.

The principle of the first degenerate DW-ACP is based on the composition of an oligonucleotide primer having 3'- and 5'-end distinct portions separated by a regulator portion comprising at least two universal base or non-discriminatory base analog residues and the effect of the regulator portion on the 3'- and 5'-end portions in the oligonucleotide primer. The presence of the regulator portion between the 3'- and 5'-end portions of the first degenerate DW-ACP acts as a main factor, which is responsible for the improvement of primer annealing specificity.

The term "nucleic acid" or "nucleotide" is a deoxyribonucleotide or ribonucleotide polymer in either single or double-stranded form, including known analogs of natural nucleotides unless otherwise indicated. Therefore, the first DW-ACP of this invention can be employed in nucleic acid amplification using a single or double-stranded gDNA, cDNA or mRNA as a template. The term "portion" used herein in conjunction with the primer of this invention refers to a nucleotide sequence separated by an intervening portion such as the regulator portion. The term "3'-end portion" or "5'-end portion" refers to a nucleotide sequence at the 3'-end or 5'-end of the primer of this invention, respectively, which is separated by the regulator portion.

The term "primer" as used herein refers to an oligonucleotide, whether occurring naturally or produced synthetically, which is capable of acting as a point of initiation of synthesis when placed under conditions in which synthesis of primer extension product which is complementary to a nucleic acid strand (template) is induced, i.e., in the presence of nucleotides and an agent for polymerization such as DNA polymerase and at a suitable temperature and pH. The primer is preferably single stranded for maximum efficiency in amplification. Preferably, the primer is an oligodeoxyribonucleotide. The primer of this invention can be comprised of naturally occurring dNMP (i.e., dAMP, dGMP, dCMP and dTMP), modified nucleotide or non-natural nucleotide.

The term "substantially complementary" in reference to primer is used herein to mean that the primer is sufficiently complementary to hybridize selectively to a nucleotide sequence under the designated annealing conditions, such that the annealed primer can be extended by polymerase to form a complementary copy of the nucleotide sequence. Therefore, this term has a different meaning from "perfectly complementary" or related terms thereof.

It has been widely known that nucleotides at some ambiguous positions of degenerate primers have been replaced by universal base or a non-discriminatory analogue such as deoxyinosine (Ohtsuka et al, 1985; Sakanari et al., 1989), 1-(2'-deoxy-beta-D-ribofuranosyl)-3-nitropyrrole (Nichols et al., 1994) and 5-nitroindole (Loakes and Brown, 1994) for solving the design problems associated with the degenerate primers because such universal bases are capable of non-specifically base pairing with all four conventional bases. However, there has not been any report that this universal base or a non-discriminatory analogue such as deoxyinosine, 1-(2'-deoxy-beta-D-ribofuranosyl)-3-nitropyrrole and 5-nitroindole can be applied to a primer for amplifying unknown nucleotide sequence, i.e., DNA walking primer, as a regulator to discriminate each functional portion of a primer in accordance with annealing temperature.

The term "universal base or non-discriminatory base analog" used herein refers to one capable of forming base pairs with each of the natural DNA/RNA bases with little discrimination between them.

According to a preferred embodiment, the universal base or non-discriminatory base analog in the regulator portion includes deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-0-methoxyethyl inosine, 2'0-methoxyethyl nebularine, 2'-0-methoxyethyl 5-nitroindole, 2'-0-methoxyethyl 4-nitro-benzimidazole, 2'-0-methoxyethyl 3-nitropyrrole and combinations thereof, but not limited to. More preferably, the universal base or non-discriminatory base analog is deoxyinosine, inosine, 1-(2'-deoxy-beta-D-ribofuranosyl)-3-nitropyrrole or 5-nitroindole, most preferably, deoxyinosine.

The presence of polydeoxynucleotides having universal bases such as deoxyinosines in a primer generates a low annealing temperature region due to its weaker hydrogen bonding interactions in base pairing. As an extension of this theory, the present inventor has induced that the presence of the polydeoxynucleotides having universal bases between the 5'-end portion and the degenerate sequence portion plus the 3'-end portion of a primer could generate a region which has a lower melting temperature, forms a boundary to each of the 5'-end portion and the degenerate sequence portion plus the 3'-end portion of the primer, and facilitates the annealing of the degenerate sequence portion plus the 3'-end portion to the target sequence at specific temperature. This theory provides the basis of the first degenerate DW-ACP of this invention.

The regulator portion in the first DW-ACP is capable of regulating an annealing portion (i.e., the degenerate random sequence and 3'-end portions) of the primer in association with annealing temperature. This regulator portion prevents annealing of the 5'-end portion sequence to a template and restricts the annealing portion of the primer to its degenerate sequence portion and 3'-end portion at the first annealing temperature. Consequently, the regulator portion dramatically improves annealing of the degenerate sequence portion plus the 3'-end portion of the first degenerate DW-ACP to the template.

In a preferred embodiment, the regulator portion of the first DW-ACP contains at least 3 universal bases or non-discriminatory base analog residues between the 5'-end portion and the degenerate sequence portion, more preferably, at least 4 universal bases or non-discriminatory base analogs. Advantageously, the universal base residues between the 5'-end portion and the degenerate sequence portion of the first degenerate DW-ACP can be up to 10 residues in length. According to one embodiment, the regulator portion of the first DW-ACP contains 3-10 universal base or non-discriminatory base analog residues. Most preferably, the universal bases between the 5'-end portion and the degenerate sequence portion of the first degenerate DW-ACP are about 3-5 residues in length. The presence of universal bases or non-discriminatory base analog residues may be contiguous or intermittent, preferably, contiguous.

The 5'-end portion of the first degenerate DW-ACP contributes partially to improve the annealing specificity. Importantly, the 5'-end portion serves alone or with other portions as a priming site in subsequent amplifications after the first round of amplification.

According to a preferred embodiment, the pre-selected nucleotide sequence of the 5'-end portion is substantially not complementary to any site on the template nucleic acid.

Generally, the 5'-end portion of the first degenerate DW-ACP contains at least 10 nucleotides in length. Preferably, the 5'-end portion sequence can be up to 60 nucleotides in length. More preferably, the 5'-end portion sequence is from 6 to 50 nucleotides, most preferably, from 18 to 25 nucleotides in length. Using a longer sequence at the 5'-end portion may reduce the efficiency of the first degenerate DW-ACP, but a shorter sequence may reduce the efficiency of annealing under high stringent conditions.

In some embodiment, the pre-selected nucleotide sequence of the 5'-end portion of the first degenerate DW-ACP can be composed of a universal primer sequence such as T3 promoter sequence, T7 promoter sequence, SP6 promoter sequence, and M13 forward or reverse universal sequence.

According to one embodiment of the present invention, some modifications in the 5'-end portion of the first degenerate DW-ACP can be made unless the modifications abolish the advantages of the DW-ACP, i.e., improvement in annealing specificity. For example, the 5'-end portion can comprises a sequence or sequences recognized by a restriction endonuclease(s), which makes it feasible to clone the amplified product into a suitable vector. In addition, the 5'-end portion can comprises at least one nucleotide with a label for detection or isolation of amplified product. Suitable labels include, but not limited to, fluorophores, chromophores, chemiluminescers, magnetic particles, radioisotopes, mass labels, electron dense particles, enzymes, cofactors, substrates for enzymes and haptens having specific binding partners, e.g., an antibody, streptavidin, biotin, digoxigenin and chelating group. The 5'-end portion also comprises bacteriophage RNA polymerase promoter region.

The degenerate random sequence portion of the first degenerate DW-ACP is present between the regulator and 3'-end portions. The term "degenerate random sequence" portion refers to a nucleotide sequence in which each nucleotide can be occupied by any one of the four deoxyribonucleotides, i.e., dATP, dTTP, dCTP, and dGTP. Thus, the degenerate random sequence portion provides a pool of primers with various nucleotide sequences, at least one of which will be anticipated to anneal to a site on an unknown target sequence of a template. For example, if the first degenerate DW-ACP comprising three degenerate nucleotides at the degenerate random sequence portion is synthesized, sixty-four distinct oligonucleotides are produced. Consequently, the use of a degenerate random sequence portion provides the first degenerate DW-ACP with more probability to hybridize to the unspecified target nucleic acid. When the target core sequence of the first degenerate DW-ACP including the degenerate sequence and 3'-end portion sequence hybridizes to a site of a template, there are several complementary binding sites of the degenerate portion and 3'-end portion sequence of the first DW-ACP present on the unknown target sequence of the template. Interestingly, the present inventor has observed that one major target product is usually generated by which the first degenerate DW-ACP binds to a target-binding site which is the nearest distance from the target-specific primer sequence of the known sequence. It may suggest that the primers being hybridized on the other binding sites, which are present on more distance from the target-specific primer sequence, are not favorable to generate any product because the extension of the primer hybridized with the nearest binding site from the target-specific primer sequence may bother the extension of the primers hybridized on the other binding sites.

The length of the degenerate random sequence portion of the first DW-ACP may be determined based on various considerable factors such as the length of the 3'-end portion, the amplification yield and the length of nucleotides to be amplified. For example, if the length of the degenerate sequence portion becomes longer, the amplification yield becomes lower in the present method. Generally, the length of the degenerate sequence portion ranges from 1 to 5, preferably 2-5, more preferably, 2-4, most preferably, 3.

The 3'-end portion of the first degenerate DW-ACP has a nucleotide sequence substantially complementary to a site on an unknown nucleotide sequence. It will be appreciated that the 3'-end portion of the first degenerate DW-ACP can have one or more mismatches to a site on the unknown nucleotide sequence to an extent that the first degenerate DW-ACP can serve as a primer. Most preferably, the 3'-end portion of the first DW-ACP has a nucleotide sequence perfectly complementary to a site on the unknown nucleotide sequence, i.e., no mismatches.

The 3'-end portion of the first degenerate DW-ACP has a nucleotide sequence to hybridize with a site on the unknown sequence, which is so-called "arbitrary" nucleotide sequence. The term "arbitrary nucleotide sequence" is used herein to mean the nucleotide sequence that is chosen without knowledge of the sequence of the unknown nucleic acids to be amplified.

Generally, the 3'-end portion of the first degenerate DW-ACP is at least 3 nucleotides in length. It is important that the annealing portion (i.e., the degenerate sequence and 3'-end portions) of the first degenerate DW-ACP is at least 6 nucleotides in length, which is considered the minimal requirement of length for primer annealing with specificity. Practically, the primer annealing with specificity could be promising with at least 8 nucleotides in the annealing portion. Preferably, the 3'-end portion sequence is from 3 to 20 nucleotides in length, more preferably, 3-10 nucleotides, and most preferably, 4-6 nucleotides.

The 3'-end portion of the first degenerate DW-ACP is prepared to have a specific arbitrary nucleotide sequence. The specific arbitrary nucleotide sequence may contain the Kozak sequence of mRNA including the translation initiation codon ATG, such as 5'-ANNATGN-3', where N is any one of the four deoxynucleotides (McBratney and Sarnow, 1996). The specific arbitrary nucleotide sequence may also contain the canonical polyadenylation signal sequence AATAAA (Juretic and Theus, 1991). Alternatively, the nucleotide at the 5'-end of the 3'-end portion of the first degenerate DW-ACP may be varied to have one of four deoxyribonucleotides, so that four types of the first degenerate DW-ACP are obtained in terms of the nucleotide sequence of the 3'-end portion.

According to a preferred embodiment, the sequences at the 3'-end in DW-ACP are chosen by considering the following factors: (1) a sequence existing at least once per 2 kb and (2) high GC ratio (preferably higher than 75%). According to a preferred embodiment, the sequence at the 3'-end portion in the first DW-ACP is GGTC or CACG.

The length of the 3'-end portion of the first degenerate DW-ACP may be determined based on various considerable factors such as the length of nucleotides to be amplified, the length of the degenerate sequence portion, and the amplification yield. For example, if the 3'-end portion has 4 arbitrary nucleotides in length, theoretically the four-base sequence combination can exist once in every 256 bp in the template. Thus, the length of nucleotides to be amplified will be more than 256 bp.

The entire first DW-ACP is preferably from 20 to 80 nucleotides in length, more preferably, 28-50 nucleotides, and most preferably, 30-40 nucleotides.

In the present method, the first target-specific primer substantially complementary to a site on the known nucleotide sequence of a template is used. The term "substantially complementary" in reference to the first target-specific primer has the same meaning as that for the first DW-ACP.

According to a preferred embodiment, the target specific primers (TSPs) have a general formula III:

$$5'-X''_p-Y''_q-Z''_r-3' \qquad (III)$$

wherein, $X''_p$ represents a 5'-high $T_m$ specificity portion having a hybridizing nucleotide sequence substantially complementary to a site on the known nucleotide sequence to hybridize therewith, $Y''_q$ represents a separation portion comprising at least two universal bases, $Z''_r$ represents a 3'-low $T_m$ specificity portion having a hybridizing nucleotide sequence substantially complementary to a site on the known nucleotide sequence to hybridize therewith, p, q and r represent the number of nucleotides, and X'', Y'', and Z'' are deoxyribonucleotide or ribonucleotide; the $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the template nucleic acid, enabling the 5'-high $T_m$ specificity portion to separate from the 3'-low $T_m$ specificity portion in terms of annealing specificity to a template nucleic acid, whereby the annealing specificity of the primer is determined dually by the 5'-high $T_m$ specificity portion and the 3'-low $T_m$ specificity portion such that the overall annealing specificity of the primer is enhanced.

The target specific primer represented by the general formula III has been newly developed by the present inventor to dramatically increase annealing specificity in amplification reactions and filed under PCT/KR2006/000746. The oligonucleotide represented by the general formula III is called "dual specificity oligonucleodite".

The term "dual specificity" with referring to the dual specificity oligonucleotide (hereinafter referred to as "DS oligo") of this invention used herein is coined to describe its prominent feature that its annealing specificity to a target sequence is dually determined by its separate two portions, i.e., the 5'-high $T_m$ specificity portion and the 3'-low $T_m$ specificity portion. In general, the annealing specificity of primers or probes is governed by their overall consecutive sequence. In contrast, the annealing specificity of the DS oligo is dually determined by its two portions (the 5'-high $T_m$ specificity portion and the 3'-low $T_m$ specificity portion) separated by the separation portion, in which these three portions are located in one oligonucleotide sequence. Such dual specificity permits the DS oligo to serve as a primer and probe exhibiting much higher specificity, rendering the present invention to be novel and unobvious over prior art.

Meanwhile, the present inventor has already developed the ACP (annealing control primer) to improve annealing specificity as disclosed in WO 03/050303, the teachings of which are incorporated herein by reference. The DS oligo of this invention is distinctly different from the ACP in light of the following: (i) the DS oligo has two specificity portions to be hybridized with a target sequence whereas the ACP has one specificity portion; (ii) three portions in the DS oligo are distinctly discriminated in view of $T_m$ whereas portions in the ACP are not; (iii) the DS primer is extended to synthesize a nucleic acid molecule complementary to the template only when annealing occurs by both the 5'-high $T_m$ specificity portion and 3'-low $T_m$ specificity portion, whereas the ACP is extended even when annealing occurs by the 3'-end portion; and (iv) thus the annealing or hybridizing specificity of the DS oligo is determined dually by the two separate portions, i.e., the 5'-high $T_m$ specificity portion and the 3'-low $T_m$ specificity portion, whereas that of the ACP is governed only by the 3'-end portion. Accordingly, it could be appreciated that the annealing or hybridizing specificity of the DS oligo to its target sequence is much higher than that that of the ACP, addressing that the DS oligo is novel and unobvious over the ACP.

The striking feature of the DS oligo is to have three different portions with distinct properties within one oligonucleotide molecule: 5'-high $T_m$ specificity portion, 3'-low $T_m$ specificity portion and separation portion.

The DS oligo is useful in a wide variety of processes and analyses involving a template-dependent extension reaction. The term used herein "a template-dependent extension reaction" means a reaction to extend an oligonucleotide molecule hybridized to a target sequence by incorporating successive nucleotides into its end moiety in which the extended sequence is determined by a complementary template sequence.

Where only the 5'-high $T_m$ specificity portion of the DS oligo is annealed to a template, it cannot serve as a priming site for a template-dependent extension, resulting in no occurrence of extension.

While the 5'-high $T_m$ specificity portion of the DS oligo is annealed to a non-target sequence, the 3'-low $T_m$ specificity portion having a shorter sequence is unlikely to anneal to the non-target sequence. The reasons for that are that the 5'-high $T_m$ specificity portion and the 3'-low $T_m$ specificity portion are separated by the separation portion in terms of annealing events. In other words, the 3'-low $T_m$ specificity portion is involved in annealing events in a relatively independent manner from the 5'-high $T_m$ specificity portion and the annealing of the 3'-low $T_m$ specificity portion is less affected by the annealing of the 5'-high $T_m$ specificity portion. In this connection, the likelihood of annealing of the 3'-low $T_m$ specificity portion to a non-target sequence becomes much lower.

Where only the 3'-low $T_m$ specificity portion has a sequence complementary to a non-target site, annealing either does not occur under certain high stringent conditions, e.g., stringent conditions for annealing of the 5'-high $T_m$ specificity portion. According to a preferred embodiment, it is advantageous to perform template-dependent extension reactions using the DS oligo under stringent conditions with annealing temperature much higher than $T_m$ of the 3'-low $T_m$ specificity portion.

Where both 5'-high $T_m$ specificity portion and 3'-low $T_m$ specificity portion have a sequence substantially complementary to a template, the DS oligo can be annealed to the template and hence the successful extension occurs.

Without wising to be bound by theory, it is believed that the separation portion makes the 3'-low $T_m$ specificity portion more sensitive to annealing conditions (e.g., temperature and sequence complementarity). In this regard, the incidence of the non-specific hybridization between the 3'-low $T_m$ specificity portion and non-target sequences becomes much lower under certain annealing (or stringent) conditions. Where the 3'-low $T_m$ specificity portion as well as the 5'-high $T_m$ specificity portion is annealed to its target sequence, the 3'-end of the 3'-low $T_m$ specificity portion is more likely to generate a site extendible by DNA polymerases.

The term "oligonucleotide" as used herein refers to a linear oligomer of natural or modified monomers or linkages, including deoxyribonucleotides, ribonucleotides and the like, capable of specifically hybridizing with a target nucleotide sequence, whether occurring naturally or produced synthetically. The oligonucleotide is preferably single stranded for maximum efficiency in hybridization. Preferably, the oligonucleotide is an oligodeoxyribonucleotide. The oligonucleotide of this invention can be comprised of naturally occurring dNMP (i.e., dAMP, dGM, dCMP and dTMP), nucleotide analogs, or nucleotide derivatives. The oligonucleotide can also include ribonucleotides. For example, the oligonucleotide of this invention may include nucleotides with backbone modifications such as peptide nucleic acid (PNA) (M. Egholm et al., *Nature*, 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

The term "portion" used herein in conjunction with the DS oligo of this invention refers to a nucleotide sequence separated by the separation portion. The term "5'-high $T_m$ specificity portion" or "3'-low $T_m$ specificity portion" refers to a nucleotide sequence at the 5'-end or 3'-end of the DS oligo of this invention, respectively, which is separated by the separation portion. The term "5'-high $T_m$ specificity portion" in conjunction with the DS oligo is intended to refer to a portion with the highest $T_m$ among three portions and having a hybridizing nucleotide sequence substantially complementary to a site on the template nucleic acid. The term "3'-low $T_m$ specificity portion" in reference to the DS oligo means a portion with a lower $T_m$ than the 5'-high $T_m$ specificity portion but higher $T_m$ than the separation portion and having a hybridizing nucleotide sequence substantially complementary to a site on the template nucleic acid.

The term "$T_m$" used herein refers to the melting temperature at which half the molecules of a nucleic acid duplex are single stranded. The terms "high $T_m$" and "low $T_m$" in conjunction with portions in the DS oligo are intended to describe a relative $T_m$ value yet not an absolute $T_m$ value. That is, it is only required that the $T_m$ of the 5'-high $T_m$ specificity portion is high relative to that of the 3'-low $T_m$ specificity portion.

The 5'-high $T_m$ specificity portion and 3'-low $T_m$ specificity portion are designed to have a hybridizing nucleotide sequence substantially complementary to a site on a template nucleic acid to hybridize therewith. The term "substantially complementary" in reference to the DS oligo is used herein to mean that the oligonucleotide molecule is sufficiently complementary to hybridize selectively to a template nucleic acid sequence under the designated annealing conditions or stringent conditions, such that the annealed oligonucleotide can be extended by a polymerase to form a complementary copy of the template. Therefore, this term has a different meaning from "perfectly complementary" or related terms thereof. It will be appreciated that the 5'-high $T_m$ specificity portion and 3'-low $T_m$ specificity portion of the DS oligo can have one or more mismatches to a template to an extent that the DS oligo can serve as primer or probe. Most preferably, the 5'-high $T_m$ specificity portion and/or 3'-low $T_m$ specificity portion of the DS oligo have a nucleotide sequence perfectly complementary to a site on a template, i.e., no mismatches.

For successful performance of the DS oligo, it is essential that the $T_m$ of the 5'-high $T_m$ specificity portion is higher than that of the 3'-low $T_m$ specificity portion. It is preferred that the $T_m$ of the 5'-high $T_m$ specificity portion ranges from 40° C. to 80° C., more preferably, 40° C. to 75° C., still more preferably, 50° C. to 68° C., and most preferably, 50° C. to 65° C. It is preferred that $T_m$ of the 3'-low $T_m$ specificity portion ranges from 10° C. to 40° C., more preferably, 15° C. to 40° C., and most preferably, 20° C. to 35° C. Preferably, the $T_m$ of the 5'-high $T_m$ specificity portion is higher at least 5° C., more preferably at least 10° C., still more preferably at least 15° C., and most preferably at least 20° C. than that of the 3'-low $T_m$ specificity portion. Advantageously, the $T_m$ of the 5'-high $T_m$ specificity portion is higher 5-70° C., preferably, 10-70° C., more preferably, 10-60° C., still more preferably, 10-50° C., still yet more preferably, 10-40° C. and most preferably, 20-40° C. than that of the 3'-low $T_m$ specificity portion.

According to a preferred embodiment, the 5'-high $T_m$ specificity portion is longer than the 3'-low $T_m$ specificity portion. The length of 5'-high $T_m$ specificity portion is preferably 15 to 40 nucleotide residues, more preferably, 15 to 30 nucleotide residues, and most preferably, 20 to 25 nucleotide residues. The length of 3'-low $T_m$ specificity portion is preferably 3 to 15 nucleotide residues, more preferably, 5 to 15 nucleotide residues, and most preferably, 6 to 12 nucleotide residues.

The separation portion comprising at least two universal bases is partly responsible for advantages and features of the DS oligo. The term "universal base" used herein refers to one capable of forming base pairs with each of the natural DNA/RNA bases with little discrimination between them.

It has been widely known that nucleotides at some ambiguous positions of degenerate primers have been replaced by universal base for solving the design problems associated with the degenerate primers, because such universal bases are capable of non-specific base pairing with all four conventional bases. However, there has not been any report that these universal bases allow forming a portion in an oligonucleotide molecule to generate a bubble structure during annealing (hybridization) or amplification and then separate two opposite adjacent sequences, resulting in the elevation of the annealing specificity of primer or probe to a target sequence by dual specificity through two separate specificity (annealing) portions.

Such universal bases may be contained in the separation portion in a contiguous manner or interrupted manner with other nucleotides such as dNMPs. It is preferable that the separation portion comprises contiguous nucleotides having universal bases, preferably, deoxyinosine.

It is critical that the separation portion in the DS oligo has the lowest $T_m$ in the three portions, in order that the separation portion forms a non base-pairing bubble structure under conditions that the 5'-high $T_m$ specificity portion and the 3'-low $T_m$ specificity portion are annealed to the template nucleic acid, enabling the 5'-high $T_m$ specificity portion to separate from the 3'-low $T_m$ specificity portion in terms of annealing specificity to the template nucleic acid, whereby the annealing specificity of the oligonucleotide is determined dually by the 5'-high $T_m$ specificity portion and the 3'-low $T_m$ specificity portion such that the overall annealing specificity of the oligonucleotide is considerably enhanced. Preferably, the $T_m$ of the separation portion ranges from 3° C. to 15° C., more preferably, 4° C. to 15° C., and most preferably 5° C. to 10° C.

According to a preferred embodiment, the separation portion between the 5'-high $T_m$ specificity portion and the 3'-low $T_m$ specificity portion contains at least 3 universal bases, more preferably at least 4 universal bases, and most preferably at least 5 universal bases. According to a preferred embodiment, the separation portion contains 2-10 universal bases, more preferably 3-10 universal bases, still more preferably, 4-8 universal bases, and most preferably, 5-7 universal bases.

Where a primer or probe having a longer sequence is required, the advantages of the DS oligo are most highlighted. For example, according to a conventional technique, a primer having a nucleotide sequence longer than 35 bp as a hybridizing sequence is very liable to generate non-specific amplicons. By contrast, the DS oligo can generate specific amplicons even with long sequences, since it carries two hybridizing sequences (i.e., the 5'-high $T_m$ specificity portion and the 3'-low $T_m$ specificity portion) separated from each other in terms of molecular interaction with templates (i.e., annealing). For example, the DS oligo may contain 35-45 bp of a hybridizing sequence complementary to a target sequence. In this regard, it could be appreciated that the present invention permits primers to be designed with much longer sequences considered to be non-practicable in conventional primer design strategies.

According to a preferred embodiment, the 5'-high $T_m$ specificity portion is 15 to 25 nucleotides in length, the separation portion is 3 to 15 nucleotides in length, and the 3'-low $T_m$ specificity portion is 3 to 15 nucleotides in length.

More preferably, the 5'-high $T_m$ specificity portion is 15 to 25 nucleotides in length; the separation portion is 3 to 10 nucleotides in length; and the 3'-low $T_m$ specificity portion is 5 to 15 nucleotides in length. Most preferably, the 5'-high $T_m$ specificity portion is 15 to 25 nucleotides in length; the separation portion is 5 to 7 nucleotides in length; and the 3'-low $T_m$ specificity portion is 6 to 10 nucleotides in length. According to the exemplary and illustrative DS oligo described in Examples, the 5'-high $T_m$ specificity portion is about 20 nucleotides in length; the separation portion is about 5 nucleotides in length; and the 3'-low $T_m$ specificity portion is about 8-10 nucleotides in length.

In the most preferred embodiment, the DS oligo is represented by the following general formula: 5'-$X''_p$-$(dI)_q$-$Z''_r$-3' (definition and characteristics of $X''_p$ and $Z''_r$ are the same as described previously, dI represents deoxyinosine, $(dI)_q$ represents a separation portion comprising contiguous nucleotides having universal bases and q is an integer between 5-7).

The primary amplification in the present invention is conducted by a two-stage amplification under different annealing temperature to take advantage of the DW-ACP system and DS oligo.

The methods of the present invention can be used to amplify any desired nucleic acid molecule. Such molecules may be either DNA or RNA. The molecule may be in either a double-stranded or single-stranded form, preferably, double-stranded. Where the nucleic acid as starting material is double-stranded, it is preferred to render the two strands into a single-stranded, or partially single-stranded, form. Methods known to separate strands includes, but not limited to, heating, alkali, formamide, urea and glycoxal treatment, enzymatic methods (e.g., helicase action) and binding proteins. For instance, the strand separation can be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y. (2001).

Where a mRNA is employed as starting material for amplification, a reverse transcription step is necessary prior to amplification, details of which are found in Joseph Sambrook, et al., *Molecular Cloning, A Laboratory Manual*, Cold Spring Harbor Laboratory Press, Cold Spring Harbor, N.Y. (2001); and Noonan, K. F. et al., *Nucleic Acids Res.* 16:10366 (1988)). For reverse transcription, an oligonucleotide dT primer hybridizable to poly A tail of mRNA is used. Reverse transcription can be done with a reverse transcriptase.

The present methods do not require that the molecules to be amplified have any particular sequence or length. In particular, the molecules which may be amplified include any naturally occurring procaryotic, eucaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleotide sequence can also be any nucleic acid molecule which has been or can be chemically synthesized. Thus, the nucleotide sequence may or may not be found in nature.

The first degenerate DW-ACP used in the present invention is hybridized or annealed to a site on the unknown nucleotide sequence so that a double-stranded structure is formed. Conditions of nucleic acid hybridization suitable for forming such double stranded structures are described by Joseph Sambrook, et al., *Molecular Cloning, A Laboratory Manual*, Cold Spring Harbor Laboratory Press, Cold Spring Harbor, N.Y.

(2001) and Haymes, B. D., et al., *Nucleic Acid Hybridization, A Practical Approach*, IRL Press, Washington, D.C. (1985). The sequence of the annealing portion (i.e., the degenerate sequence and 3'-end portions) of the first DW-ACP needs not to exhibit precise complementarity, but need only to be substantially complementary in sequence to be able to form a stable double-stranded structure. Thus, departures from complete complementarity are permissible, so long as such departures are not sufficient to completely preclude hybridization to form a double-stranded structure. Hybridization of the first DW-ACP to a site on the unknown sequence is a prerequisite for its template-dependent polymerization with polymerases. Factors (see Joseph Sambrook, et al., *Molecular Cloning, A Laboratory Manual*, Cold Spring Harbor Laboratory Press, Cold Spring Harbor, N.Y. (2001); and Haymes, B. D., et. al., *Nucleic Acid Hybridization, A Practical Approach*, IRL Press, Washington, D.C. (1985)) which affect the base pairing of the first DW-ACP to its complementary nucleic acids subsequently affect priming efficiency. The nucleotide composition of the first degenerate DW-ACP can affect the temperature at which annealing is optimal and therefore can affect its priming efficiency.

A variety of DNA polymerases can be used in the amplification step of the present methods, which includes "Klenow" fragment of *E. coli* DNA polymerase I, a thermostable DNA polymerase and bacteriophage T7 DNA polymerase. Preferably, the polymerase is a thermostable DNA polymerase such as may be obtained from a variety of bacterial species, including *Thermus aquaticus* (Taq), *Thermus thermophilus* (Tth), *Thermus filiformis*, *Thermis flavus*, *Thermococcus literalis*, and *Pyrococcus furiosus* (Pfu). When a polymerization reaction is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired.

All of the enzymes used in this amplification reaction may be active under the reaction conditions. Indeed, buffers exist in which all enzymes are near their optimal reaction conditions.

Two amplification stages of the present method are separated only in time. The first-stage amplification should be followed by the second-stage amplification. Therefore, the two-stage amplification can be conducted in a reaction including all types of primers, the first DW-ACP and the first target-specific primer.

Annealing or hybridization in the two-stage amplification is performed under stringent conditions that allow for specific binding between a nucleotide sequence and the primers. Such stringent conditions for annealing will be sequence-dependent and varied depending on environmental parameters. In the present methods, it is preferred that two amplification stages are carried out under different conditions, inter alia, at different annealing temperature each other. Preferably, the annealing in the first-stage amplification is performed under low stringent condition, inter alia, at low annealing temperature. More preferably, the first annealing temperature is between about 35° C. and 50° C., and most preferably, 40-48° C. At the first annealing temperature, the annealing portion of the first DW-ACP is restricted to the degenerate sequence and 3'-end portions, thereby improving annealing specificity.

According to the present method, the first-stage amplification under low stringent conditions is carried out for at least one cycle of annealing, extending and denaturing to improve the specificity of primer annealing during the first-stage amplification, and through the subsequent cycles, the second-stage amplification is processed more effectively under high stringent conditions. It is most preferred that the first-stage amplification is carried out for one cycle. One cycling of the first-stage amplification may be important because it could fundamentally prevent the first degenerate DW-ACP alone from generating non-specific amplification products. During the one cycle of the primary amplification (first-stage amplification), the 3'-end portion of the first DW-ACP binds to the unknown target sites of the template under such low stringent conditions. However, during the next cycles of the primary amplification (second-stage amplification) under high stringent conditions, e.g., higher annealing temperature, only the 3' end portion of the first DW-ACP no longer plays as a primer to bind to the template or the extended primer sequence. Instead, all portions of the first DW-ACP as well as the first TSP are involved in the second-stage amplification to generate the primary amplification product.

The second-stage amplification is preferably performed under high stringent condition, inter alia, at high annealing temperature. Advantageously, the second annealing temperature is between about 50° C. and 72° C., more preferably, 50-65° C., and most preferably, 52-65° C. At a high annealing temperature such as the second annealing temperature, only the 3'-end portion of the first degenerate DW-ACP no longer serves as a primer; instead, all portions of the first DW-ACP and the first TSP work as a primer with higher specificity.

The second-stage amplification under high stringent conditions is carried out for at least one cycle, preferably, at least 5 cycles to generate the primary amplification product without degenerate random nucleotide sequence derived from the first degenerate DW-ACP. In a more preferred embodiment, the second-stage amplification is carried out for 10-40 cycles, more preferably, 10-30 cycles, and most preferably, 10-20 cycles.

High and low stringent conditions may be readily determined from the standard known in the art. "Cycle" refers to the process which results in the production of a copy of target nucleic acid. A cycle includes a denaturing step, an annealing step, and an extending step.

In the most preferable embodiment, the amplification is performed in accordance with PCR which is disclosed in U.S. Pat. Nos. 4,683,195, 4,683,202, and 4,800,159.

In the second-stage amplification of the primary amplification reaction, the first TSP is annealed to its complementary sequence on the known nucleotide sequence to generate a target-specific primer extension product. If the regulator portion of the first degenerate DW-ACP comprises universal bases or non-discriminatory base analogs, its opposite strand on the target-specific primer extension product comprises the nucleotides preferably recognized by DNA polymerase as described hereinabove. For example, where the regulator portion of the first degenerate DW-ACP comprises at least two deoxyinosine or inosine residues, at least 2 deoxycytidine nucleotides are incorporated into its opposite strand on the target-specific primer extension product.

Meanwhile, the present inventor had developed similar process to the present invention and filed a PCT application (WO 2005/045073). The previously developed process uses a second DW-ACP rather than the first DW-ACP at the second-stage amplification of the primary amplification. Therefore, the second-stage amplification contains two types of the DW-ACP, which renders the adjustment of amplification conditions to be complicated. In addition, WO 2005/045073 does not disclose target specific primers having the dual specificity oligonucleotide structure to dramatically enhance annealing specificity.

According to a preferred embodiment, the present method further comprises the step of (b) performing a secondary amplification at a third annealing temperature, comprising at least one cycle of primer annealing, primer extending and denaturing, using (i) a second DW-ACP having a nucleotide sequence to hybridize with the opposite-sense nucleotide sequence to the first degenerate DW-ACP sequence present at the 3'-end of the primary amplification product or a primer having a nucleotide sequence corresponding to the 5'-end portion of the first degenerated DW-ACP and (ii) a second nested TSP designed to amplify an internal region of the primary amplification product.

The second DW-ACP used in the secondary amplification reaction is preferably represented by a general formula II:

$$5'\text{-}X'_p\text{-}S_u\text{-}Y'_v\text{-}Z'_w\text{-}3' \quad (II)$$

wherein, $X'_p$ represents a 5'-end portion having a nucleotide sequence corresponding to the 5'-end portion of the first degenerate DW-ACP, $S_u$ represents a supplementary annealing portion comprising a nucleotide sequence to hybridize with a portion opposite to the regulator portion of the first degenerate DW-ACP in the primary amplification product of the step (a-2), $Y'_v$ represents a regulator portion comprising at least two universal base or non-discriminatory base analog residues and prevents annealing of said $X'_p$ and $S_u$ portions to non-target sequences except to the nucleotide sequence complementary to the first degenerate DW-ACP, $Z'_w$ represents a 3'-end portion having a nucleotide sequence corresponding to the 3'-end portion of the first degenerate DW-ACP, p, u, v and w represent the number of nucleotides, and X', S, Y', and Z' are deoxyribonucleotide or ribonucleotide.

The term "corresponding to" used herein with reference to two related nucleotide sequences is intended to express both perfectly and partially identical sequences to an extent that the one nucleotide sequence can be hybridized with a nucleotide sequence hybridizable with the other comparative nucleotide sequence.

The second DW-ACP of the formula III has a nucleotide sequence corresponding to that of the first degenerate DW-ACP. The primer of the formula III exhibits much higher annealing specificity.

The 5'-end portion of the second DW-ACP has a nucleotide sequence corresponding to the 5'-end portion of the first DW-ACP. That is, the nucleotide sequence of the 5'-end portion of the second DW-ACP may be completely identical or partially identical to that of the 5'-end of the first DW-ACP. Departures from complete identity are permissible, so long as such departures are not sufficient to completely preclude hybridization to form a double-stranded structure between the 5'-end portion of the second DW-ACP and the nucleotide sequence with the opposite sense to the 5'-end portion of the first DW-ACP.

The supplementary annealing portion ($S_u$) is very unique in the second DW-ACP of the formula III, which is partially responsible for the complete removal of the high background problem resulting from the non-specific binding of primer to non-specific sites. The supplementary annealing portion comprises a nucleotide sequence to hybridize with a portion opposite to the regulator portion of the first degenerate DW-ACP. This strategy for designing the supplementary annealing portion employs the recognition of universal base by DNA polymerase (e.g., Taq polymerase) to direct the incorporation of natural dNMPs. The recognition of universal base by DNA polymerase has been reported by Geoffrey C. Hoops, et al. (*Nucleic Acids Research*, 25(24):4866-4871 (1997)), which is incorporated herein by reference. For example, 8-hydroxyguanie, 2-hydroxyadenine, 6-O-methylguanine and xanthine direct the incorporation of (C and A), (T and A), (T and C) and (T and C), respectively. Furthermore, Geoffrey C. Hoops, et al have resulted that a base having nitropyrrole and inosine direct most preferably the incorporation of dAMP and dCMP, respectively.

Therefore, if the regulator portion of the first degenerate DW-ACP comprises at least two deoxyinosine or inosine residues, the supplementary annealing portion should comprise at least 2 deoxyguanosine nucleotides because deoxycytidine nucleotides are most preferably incorporated into the portion opposite to the regulator portion by Taq polymerase.

In the second DW-ACP, $Y'_v$, a regulator portion, prevents annealing of the $X'_p$ and $S_u$ portions to non-target sequences except to the sequence complementary to the first DW-ACP. Furthermore, the regulator portion provides an additional annealing portion by way of the indiscriminative binding of universal bases or non-discriminatory base analogs such that the second DW-ACP is able to selectively anneal to the sequences complementary to the first degenerate DW-ACP sequences in the resultant products.

The regulator portion of the formula III is hybridized with a portion opposite to the degenerate sequence portion of the first degenerate DW-ACP. The universal base or non-discriminatory base analog suitable in regulator portion may include any base to show loss of discrimination when participating in DNA replication known in the art.

The length of the regulator portion of the formula III is mainly determined by that of the degenerate sequence portion of the first degenerate DW-ACP. Furthermore, if the nucleotide at the 5'-end of the 3'-end portion of the first degenerate DW-ACP is designed to have a specific nucleotide from four deoxyribonucleotides, the regulator portion becomes longer by 1 nucleotide. The universal bases in the regulator portion of the formula III exist preferably in a contiguous arrangement.

The 3'-end portion in the second DW-ACP has a nucleotide sequence corresponding to the 3'-end portion of the first degenerate DW-ACP. The nucleotide sequence of the 3'-end portion of the second DW-ACP may be completely or partially identical to that of the 3'-end of the first DW-ACP. Departures from complete identity are permissible, so long as such departures are not sufficient to completely preclude hybridization to form a double-stranded structure between the 3'-end portion of the second DW-ACP and the nucleotide sequence with the opposite sense to the 3'-end portion of the first DW-ACP. Most preferably, the nucleotide sequence of the 3'-end portion of the second DW-ACP is completely identical to that of the 3'-end of the first DW-ACP because the perfect match of the 3'-end portion of the primer to template is required for a successful amplification.

The primer having a nucleotide sequence corresponding to the 5'-end portion of the first degenerated DW-ACP may be used instead of the second DW-ACP in the secondary amplification.

The secondary amplification follows a nested amplification process known in the art for selectively amplifying an unknown target product from the primary amplification products. The second nested TSP is designed to amplify an internal region of the primary amplification product. According to a preferred embodiment, the second nested TSP is constructed to have the DS oligo structure represented by the general formula III.

The secondary amplification is preferably performed under a high stringent condition, inter alia, at high annealing temperature. Advantageously, the high annealing temperature is between about 50° C. and 72° C., more preferably, 50-70° C., and most preferably, 55-68° C. At a high annealing temperature, all portions, not a portion, of the second DW-ACP are involved in annealing. Therefore, the second DW-ACP is able to anneal exclusively to a nucleotide sequence complementary to the second DW-ACP. The secondary amplification under high stringent conditions is carried out for at least one cycle, preferably, at least 5 cycles to amplify the primary amplification product. In a more preferred embodiment, the secondary amplification is carried out for 10-40 cycles.

In the most preferable embodiment, the secondary amplification is performed in accordance with PCR which is disclosed in U.S. Pat. Nos. 4,683,195, 4,683,202 and 4,800,159.

The secondary amplification gives rise to amplified products having no the degenerate random sequence derived from the first DW-ACP. Where the third amplification is followed by the secondary amplification, the elimination of degenerate random sequence on the secondary amplification product ensures the third amplification to perform with more specificity and reliability.

Where the desired results to completely overcome non-specific amplification is not accomplished or is doubtable, or where the amplified products of step (b) were not visible on agarose gels, the nested amplification may be further performed for at least 1 cycle with another target-specific primer designed to amplify an internal region of the secondary amplification product.

According to a preferred embodiment, the present method further comprises the step of (c) performing a third amplification at a fourth annealing temperature, comprising at least one cycle of primer annealing, primer extending and denaturing, using (i) the second DW-ACP or a primer having a nucleotide sequence corresponding to the 5'-end portion of the first degenerated DW-ACP and (ii) a third nested TSP designed to amplify an internal region of the secondary amplification product.

According to a preferred embodiment, the present method further comprises the step (a') of purifying a reaction resultant of the step (a) to remove the first degenerate DW-ACP, the second DW-ACP and the first target-specific primer prior to performing the step (b). For example, the purification of amplified product can be accomplished by gel electrophoresis, column chromatography, affinity chromatography or hybridization. It is most preferable that the purification be carried out using a spin column with silica-gel membrane. This method employs the selective binding properties of a silica-gel membrane to which the amplified products are adsorbed in the presence of high salt, while contaminants such as primer pass through the column. Therefore, the amplified products are quickly purified and obtained from the amplification reactions.

In another aspect of this invention, there is provided a target specific primer used for a method for amplifying an unknown nucleotide sequence adjacent to a known nucleotide sequence, which is represented by the following general formula III:

$$5'\text{-}X''_p\text{-}Y''_q\text{-}Z''_r\text{-}3' \quad \text{(III)}$$

wherein, $X''_p$ represents a 5'-high $T_m$ specificity portion having a hybridizing nucleotide sequence substantially complementary to a site on the known nucleotide sequence to hybridize therewith, $Y''_q$ represents a separation portion comprising at least two universal bases, $Z''_r$ represents a 3'-low $T_m$ specificity portion having a hybridizing nucleotide sequence substantially complementary to a site on the known nucleotide sequence to hybridize therewith, p, q and r represent the number of nucleotides, and X", Y", and Z" are deoxyribonucleotide or ribonucleotide; the $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the template nucleic acid, enabling the 5'-high $T_m$ specificity portion to separate from the 3'-low $T_m$ specificity portion in terms of annealing specificity to a template nucleic acid, whereby the annealing specificity of the primer is determined dually by the 5'-high $T_m$ specificity portion and the 3'-low $T_m$ specificity portion such that the overall annealing specificity of the primer is enhanced.

Since the target specific primer (TSP) of this invention is employed in the amplification process of this invention described above, the common descriptions between them are omitted in order to avoid the complexity of this specification leading to undue multiplicity.

In still another aspect of this invention, there is provided a kit used for a method for amplifying an unknown nucleotide sequence adjacent to a known nucleotide sequence, which comprises the target specific primer having the general formula III described above.

According a preferred embodiment, the present kit may further comprise the first degenerate DW-ACP and/or the second DW-ACP. The present kits may optionally include the reagents required for performing DNA amplification such as buffers, DNA polymerase, DNA polymerase cofactors, and deoxyribonucleotide-5'-triphosphates. Optionally, the kits may also include various polynucleotide molecules, reverse transcriptase, various buffers and reagents, and antibodies that inhibit DNA polymerase activity. Optimal amounts of reagents to be used in a given reaction can be readily determined by the skilled artisan having the benefit of the current disclosure. The kits, typically, are adapted to contain in separate packaging or compartments the constituents afore-described.

The subject invention can provide an improved method for selectively amplifying an unknown nucleotide sequence from a nucleic acid or a mixture of nucleic acids (DNA or mRNA) by performing nucleic acid amplifications, preferably, PCR.

The present invention can be applied to a variety of nucleic acid amplification-based technologies. Representative examples are:

(i) genome walking for obtaining series of unknown DNA regions on either side of chromosomal regions of known nucleotide sequence. Examples are genome sequencing projects, cloning of promoter region, identification of gene structure such as exon/intron junction, gap filling, and location or orientation of transgene;

(ii) rapid amplification of 5'- and 3'-Ends of cDNA (RACE) for cloning or sequencing full-length cDNA of cDNA or for splicing analysis;

(iii) mapping of regions containing deletions, insertions, and translocations; and (iV) rapid amplification of BAC ends without shotgun cloning for whole genome sequencing.

The following specific examples are intended to be illustrative of the invention and should not be construed as limiting the scope of the invention as defined by appended claims.

EXAMPLES

Example 1

Determination of Transgene Location

To demonstrate the application of the DNA walking ACP-DSO PCR method of the subject invention, the peripheral blood stem cells (PBSCs) were infected with retrovirus MFG-GFP and the location of the transgene was determined.

A. Primer Design

A-1: DNA walking annealing control primers (DW-ACPs)

DNA walking annealing control primers (DW-ACPs) were designed for amplifying an unknown sequences adjacent to the transgene. The DW-ACP was in a tripartite structure having a polydeoxyinosine [poly(dI)] linker between the 3'-end target binding sequence and the 5'-end non-target tail sequence, wherein the 3'-end target binding sequence comprises a predetermined arbitrary sequence at its 3'-end and a degenerate random sequence at its 5'-end, and one of nucleotides A, C, T and G between the 3'- and 5'-ends of the 3'-end portion. Therefore, at least four different DW-ACP primers will be generated depending on the arbitrary sequence at the 3'-end of the 3'-end portion of the DW-ACP.

Four different degenerate DNA walking annealing control primers (DW-ACPs), wherein the annealing control primer (ACP) has been developed by the present inventor and disclosed in WO 03/050305, were designed as follows:

```
DW-ACP1-A:                              (SEQ ID NO: 1)
5'-TCACAGAAGTATGCCAAGCGAIIIINNNACACG-3';

DW-ACP1-C:                              (SEQ ID NO: 2)
5'-TCACAGAAGTATGCCAAGCGAIIIINNNCCACG-3';

DW-ACP1-T:                              (SEQ ID NO: 3)
5'-TCACAGAAGTATGCCAAGCGAIIIINNNTCACG-3'; and DW-ACP1-G:                              (SEQ ID NO: 4)
5'-TCACAGAAGTATGCCAAGCGAIIIINNNGCACG-3'.
```

In the degenerate DW-ACPs, CACG (corresponding to the 3'-end portion of the first degenerate DW-ACP) was chosen as a predetermined arbitrary sequence. The predetermined arbitrary sequences at the 3'-end in DW-ACP are chosen by considering the following factors: (1) a sequence exists at least once per 2 kb and (2) GC ratio of the sequence is preferably higher than 75%. In addition, the sequence, CACG was chosen in the senses that it was not included in the upstream of binding sites of TSPs (target specific primers) described in A-2.

Second DNA walking annealing control primers (second DW-ACP) or universal primers were used in the secondary amplification.

Second DNA walking annealing control primers (second DW-ACP) were designed as follows:

```
DW-ACP2-N:                              (SEQ ID NO: 5)
5'-TCACAGAAGTATGCCAAGCGAGGGGIIIICACG-3';
```

The sequence of the second DW-ACP was designed to exclusively anneal to the sequences completely complementary to all of the pool of the first degenerate DW-ACPs, not any other non-target sites of a template due to the feature of ACP structure.

The universal primer corresponding to the 5'-end portion sequence of the DW-ACPs is as follows:

```
                                        (SEQ ID NO: 6)
Universal primer: 5'-TCACAGAAGTATGCCAAGCGA-3'.
```

A-2: Target Specific Primers (TSP) Design

Target specific primers were designed by considering the retroviral region (transgene).

```
MFG-TSP1:                               (SEQ ID NO: 7)
5'-CGAAGTCCCTGGGACGTCTCCCAGGGTTGC-3';

MFG-TSP2:                               (SEQ ID NO: 8)
5'-GTCAGTTCCACCACGGGTCCGCCAGATACAGAGCTA-3'; and MFG-TSP3:                               (SEQ ID NO: 9)
5'-ATAAGGCACAGGGTCATTTCAG-3'.
```

MFG-TSP1 and MFG-TSP2 were chosen from the gag gene region, and MFG-TSP3 was chosen from the 5'-LTR region of target retrovirus.

The structure of the Dual Specificity Oligouncleotides (DSO) developed by the present inventor was applied to designing TSPs, thereby dramatically enhancing the annealing specificity.

The following dual specificity oligonucleotide primers (DSOs) comprise the separation portion having a polydeoxyinosine [poly(dI)] linker between their 5'-end portion and 3'-end portion. Furthermore, the DS primers are designed to comprise a 5'-high $T_m$ specificity portion and a 3'-low $T_m$ specificity portion in a way that $T_m$ of the 5'-high $T_m$ specificity portion is higher than that of the 3'-low $T_m$ specificity portion, while the separation portion has the lowest $T_m$ among the three portions.

Target specific dual specificity primers (DSO-TSPs) were designed as follows:

```
MFG-DSO-TSP1:                           (SEQ ID NO: 10)
5'-CGAAGTCCCTGGGACGIIIIICAGGGTTGC-3'; and MFG-DSO-TSP2:                           (SEQ ID NO: 11)
5'-GTCAGTTCCACCACGGGTCCIIIIIATACAGAGCTA-3';
```

B. Genomic DNA Preparation

Normal human CD34⁺ peripheral blood stem cells (PBSCs) infected with retrovirus MFG-GFP were provided from Dr. Choi Eui-Mook (NIH). The genomic DNA was purified and used as the PCR template.

C. Primary PCR

Primary PCR was conducted by a two-stage PCR amplification in four individual tubes each of which contains one of the degenerated DW-ACPs and first target specific primer (DSO-TSP1).

The two-stage PCR amplification was conducted at two different annealing temperatures in a final volume of 50 μl containing 50 ng of the PBSC genomic DNA, 25 μl of 2× SeeAmP™ ACP™ Master mixII (E1012), 4 μl of one of the DW-ACPs (2.5 μM) and 1 μl of target specific primer (MFG-DSO-TSP1 (10 μM)); the tube containing the reaction mixture was placed in a preheated (94° C.) thermal cycler; the first-stage PCR reaction consists of one cycle of 94° C. for 5 min, 40-45° C. for 1 min, and 72° C. for 2 min, followed by the second stage-PCR reaction by 10-30 cycles of 94° C. for 30 sec, 55-60° C. for 30 sec, and 72° C. for 100 sec, and followed by a 5 min final extension at 72° C.

D. Purification of Primary PCR Products

To remove primers such as the degenerated DW-ACPs and first DSO-TSP used in the primary PCR, the first amplification products were purified using a spin column (PCR purification Kit, QIAGEN).

E. Secondary PCR o amplify only an unknown target-specific product from the primary PCR products that might have non-specific products due to the non-specific priming of the primers used in primary PCR, a secondary PCR was conducted using the second DW-ACP2-N or universal primer and a nested target-specific primer (MFG-DSO-TSP2) designed to amplify an internal region of the primary PCR product. The secondary PCR amplification was conducted in a final volume of 20 μl containing 1-5 μl of the primary PCR amplification products, 10 μl of 2× SeeAmp™ ACP™ Master mixII (E1012), 1 μl of the second DW-ACP-N or universal (2.5 μM), and 1 μl of the nested target specific primer (MFG-TS-DSP2, (10 μM)); the tube containing the reaction mixture was placed in a preheated (94° C.) thermal cycler; the PCR reactions consist of denaturing 94° C. for 5 min, followed by 20-35 cycles of 94° C. for 30 sec, 55-65° C. for 30 sec, and 72° C. for 100 sec, and followed by a 5 min final extension at 72° C.

If the secondary amplification products are not visible on agarose gels, the third amplification is further performed using another nested target-specific primer, MFG-TSP3 designed to amplify an internal region of the secondary amplification product with the universal primer. The third PCR amplification was conducted in a final volume of 20 μl containing 1-5 μl of the primary PCR amplification products, 10 μl of 2× SeeAmP™ ACP™ Master mixII (E1012), 1 μl of the universal primer (2.5 μM), and 1 μl of the nested target specific primer (MFG-TSP3, (10 μM)); the tube containing the reaction mixture was placed in a preheated (94° C.) thermal cycler; the PCR reactions consist of denaturing 94° C. for 5 min, followed by 20-35 cycles of 94° C. for 30 sec, 55-65° C. for 30 sec, and 72° C. for 100 sec, and followed by a 5 min final extension at 72° C.

F. Gel Extraction

The amplified products were analyzed by electrophoresis on a 2% agarose gel and detected by staining with ethidium bromide. The resulting PCR products can be also detected on a denaturing polyacrylamide gel by autoradiography or non-radioactive detection methods. After electrophoresis on agarose gel stained with EtBr, each PCR product was extracted using GENECLEAN II Kit (Q-BIOgene, USA).

G. Cloning or Sequencing

The extracted fragments were cloned into pCR2.1-TOPO vector (Invitrogen, USA) as described by the manufacturer. The plasmids were transformed to the TOP10 competent cell. The transformed cells were plated on LB/ampicillin agar plates. The plasmids were isolated from single and white colonies. The inserts were confirmed by digestion with EcoR1 restriction enzyme. The plasmid with the insert was sequenced using ABI PRISM 310 genetic analyzer (Applied Biosystems, USA). Alternatively, the extracted fragments were used as templates for direct sequencing by the ABI PRISM 310 Genetic Analyzer (Perkin-Elmer Corp., Norwalk, Conn.) using BigDye Terminator cycle sequencing kit (Perkin-Elmer Corp.). Computer-assistant sequence analysis was carried out using the GeneRunner program (Hastings, Inc.).

Figure 2:
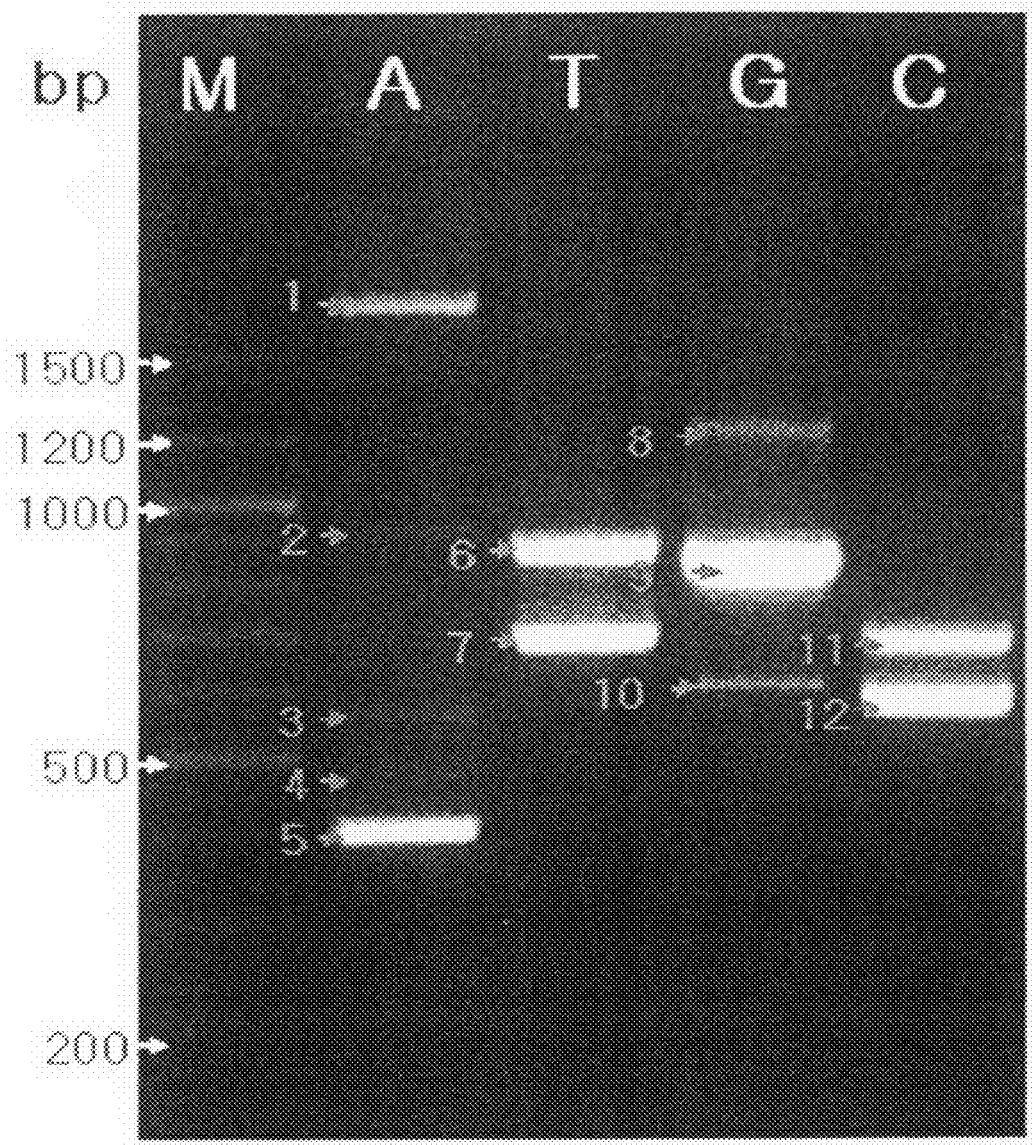
FIG. 2 shows the amplified products generated by DNA walking ACP-DSO PCR for the amplification of human genome DNA sequences adjacent to a transgene originated from the retrovirus MFG. Lane M denotes 100 bp DNA ladder. Lanes A, T, G and C represent the results from amplifications using DW-ACP1-A, DW-ACP1-T, DW-ACP1-G and DW-ACP1-C, respectively.

FIG. 2 shows the amplified products generated by DNA walking ACP-DSO PCR for the amplification of DNA sequences adjacent to the transgene. Several major products with a different size were generated by each different first DW-ACPs, DW-ACP-A (lane 1), DW-ACP-T (lane 2), DW-ACP-G (lane 3), and DW-ACP-C (lane 4).

Each band indicated in FIG. 2 was cloned and sequenced. Sequencing results show that 5'-LTR sequences were included in all the clones. Also, it was turned out that the cloned PCR products contained the host genomic DNA sequence.

The insertion sites of retrovirus MFG-GFP were determined using the UCSC genome browser with the sequencing results of the cloned PCR products.

FIG. 3 summarizes results of the identification of MFG insertion sites. The cloned PCR products were named as DW# corresponding to the indicated band numbers in FIG. 2.

Where DSO-TSP1 was used in the primary PCR, the amplification results were obtained at satisfying level in the secondary PCR. The third PCR results were almost similar to those of the secondary PCR. Accordingly, it could be appreciated that DSO-TSP permits to obtain amplification results at satisfying level within secondary PCR.

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Arnold, C., Hodgson, I. J. (1991) Vectorette PCR: a novel approach to genomic walking. PCR Methods Appl. 1:39-42.

Chun, J. Y. (2001) Annealing control primers and its uses. PCT/KR02/01781.

Dominguez, O., Lopez-Iarrea, C. (1994) Gene walking by unpredictably primed PCR. *Nucleic Acids Res*. 22:3247-3248.

Hwang, I. T., Kim, Y. H., Kim, S. H., Kwak, C. I, Gu, Y. Y., Chun, J. Y. (2003) Annealing control primer system for improving specificity of PCR amplification. *BioTechniques* (in press).

Hwang, I. T., Lee, Y. H., Moon, B. C., Ahn, K. Y., Lee, S. W., Chun, J. Y. (2000) Identification and characterization of a new member of the placental prolactin-like protein-C (PLP-C) subfamily, PLP-Cβ. *Endocrinology* 141:3343-3352.

Iwahana, H., Tsujisawa, T., Katashima, R., Yoshimoto, K., Itakura, M. (1994) PCR with end trimming and cassette ligation: a rapid method to clone exon-intron boundaries and a 5'-upstream sequences of genomic DNA based on a cDNA sequence. PCR Methods Appl. 4:19-25.

Jones, D. H., Winistorfer, S. C. (1997) Amplification of 4-9 kb human genomic DNA flanking a known site using a panhandle PCR variant. *BioTechniques* 23:132-138.

Juretic, N, Theus, M. (1991) Analysis of the polyadenylation consensus sequence context in the genes of nuclear encoded mitochondrial proteins. *FEBS Lett*. 290:4-8.

Kilstrup, M., Kristinansen, K. N. (2000) Rapid genome walking: a simplified oligo-cassette mediated polymerase chain reaction using a single genome-specific primer. *Nucleic Acids Res*. 28:e55.

Lagerstrom, M., Parik, J., Malmgren, H., Stewart, J., Pettersson, U., Landegren, U. (1991) Capture PCR: efficient amplification of DNA fragments adjacent to a known sequence in human and YAC DNA. PCR Methods Appl. 1:111-119.

McBratney, S., Sarnow, P. (1996) Evidence for involvement of trans-acting factors in selection of the AUG start codon during eukaryotic translation initiation. *Mol Cell Biol*. 16:3523-3534.

Riley, J., Butler, R., Ogilvie, D., Finnear, R., Jenner, D., Powell, S., Anand, R., Smith, J. C., Markham, A. F. (1990) A novel, rapid method for the isolation of terminal sequences from yeast artificial chromosome (YAC) clones. *Nucleic Acids Res*. 18:2887-2890.

Rosenthal, A., Jones, D. S. C. (1990) Genomic walking and sequencing by oligo-cassette mediated polymerase chain reaction. *Nucleic Acids Res.* 18:3095-3096.

Roux, K. H., Dhanarajan, P. (1990) A strategy for single site PCR amplification of dsDNA: priming digested cloned or genomic DNA from an anchor-modified restriction and a short internal sequence. *BioTechniques* 8:48-57.

Shyamala, V., Ames, G. F. L. (1989) Genome walking by single-specific primer polymerase chain reaction: SSP-PCR. *Gene* 84:1-8.

Siebert, P. D., Chenchik., A., Kellogg., D. E., Lukyanov, K. A., Lukyanov, S. A. (1995) An improved PCR method for walking in uncloned genomic DNA. *Nucleic Acids Res.* 23:1087-1088.

Triglia, T., Peterson, M. G, Kemp, D. J. (1988) A procedure for in vitro amplification of DNA segments that lie outside the boundaries of known sequences. *Nucleic Acids Res.* 16: 8186.

Trueba, G. A., Johnson, R. C. (1996) Random primed genome walking PCR: a simple procedure to retrieve nucleotide fragments adjacent to known DNA sequences. *BioTechniques* 21:20.

Willems, H. (1998) Adaptor PCR for the specific amplification of unknown DNA fragments. *BioTechniques* 24:26-28.

What is claimed is:

1. A method for amplifying an unknown nucleotide sequence adjacent to a known nucleotide sequence, which comprises the step of (a) performing a primary amplification of the unknown nucleotide sequence using a DNA walking annealing control primer (DW-ACP) and a first target specific primer (TSP) hybridizable with a site on the known nucleotide sequence, and the step of (b) performing a secondary amplification; in which the step (a) comprises:

(a-1) performing a first-stage amplification of the unknown nucleotide sequence at a first annealing temperature, said first-stage amplification comprising at least one cycle of primer annealing, primer extending, and denaturing, using a first degenerate DW-ACP containing (i) a degenerate random nucleotide sequence to hybridize with the unknown nucleotide sequence and (ii) a hybridizing nucleotide sequence substantially complementary to a site on the unknown nucleotide sequence, wherein the first annealing temperature enables the first degenerate DW-ACP to function as a primer, whereby a first degenerate DW-ACP extension product is generated; and (a-2) performing a second-stage amplification of the amplification product generated from step (a-1) at a second annealing temperature which is higher than the first annealing temperature, comprising at least one cycle of primer annealing, primer extending, and denaturing using the first degenerate DW-ACP as used in the step (a-1) and the first TSP, under conditions in which each primer anneals to its target nucleotide sequence, whereby a primary amplification product is generated;

wherein the first degenerate DW-ACP has the general formula I:

         (I)

wherein, $X_p$ represents a 5'-end portion having a pre-selected nucleotide sequence, $Y_q$ represents a regulator portion comprising at least two universal base or non-discriminatory base analog residues, $Z_r$ represents a degenerate random sequence portion having a degenerated random nucleotide sequence, $Q_s$ represents a 3'-end portion having a hybridizing nucleotide sequence substantially complementary to a site on said unknown nucleotide sequence to hybridize therewith, p, q, r, and s represent the number of nucleotides, and X, Y, Z, and Q are deoxyribonucleotide or ribonucleotide; and in which the step (b) comprises performing a secondary amplification at a third annealing temperature, said secondary amplification comprising at least one cycle of primer annealing, primer extending, and denaturing, using (i) a second DW-ACP and (ii) a second TSP designed to amplify an internal region of the primary amplification product;

wherein the second DW-ACP has the general formula II:

         (II)

wherein, $X'_p$ represents a 5'-end portion having a nucleotide sequence corresponding to the 5'-end portion of the first degenerate DW-ACP, $S_u$ represents a supplementary annealing portion comprising a nucleotide sequence to hybridize with a portion opposite to the regulator portion of the first degenerate DW-ACP in the primary amplification product of the step (a-2), $Y'_v$ represents a regulator portion comprising at least two universal base or non-discriminatory base analog residues and prevents annealing of said $X'_p$ and $S_u$ portions to sequences except for the nucleotide sequence complementary to the first degenerate DW-ACP, $Z'_w$ represents a 3'-end portion having a nucleotide sequence corresponding to the 3'-end portion of the first degenerate DW-ACP, p, u, v, and w represent the number of nucleotides, and X', S, Y', and Z' are deoxyribonucleotide or ribonucleotide.

2. The method according to claim 1, wherein said first-stage amplification is performed for one cycle.

3. The method according to claim 1, wherein the second-stage amplification is performed for at least 5 cycles.

4. The method according to claim 1, wherein said first annealing temperature is between about 35° C. and 50° C.

5. The method according to claim 1, wherein said second annealing temperature is between about 50° C. and 72° C.

6. The method according to claim 1, wherein the method further comprises the step (a') of purifying a reaction resultant of the step (a) to remove the first degenerate DW-ACP and the first target-specific primer prior to performing the step (b).

7. The method according to claim 1, wherein the method further comprises the step of (c) performing a third amplification at a fourth annealing temperature, comprising at least one cycle of primer annealing, primer extending and denaturing, using (i) the second DW-ACP or a primer having a nucleotide sequence corresponding to the 5'-end portion of the first degenerate DW-ACP and (ii) a third TSP designed to amplify an internal region of the secondary amplification product.

8. The method according to claim 1, wherein the first and/or second TSPs have a general formula III:

$$5'\text{-}X''_p\text{-}Y''_q\text{-}Z''_r\text{-}3' \quad \text{(III)}$$

wherein, $X''_p$ represents a 5'-high $T_m$ specificity portion having a hybridizing nucleotide sequence substantially complementary to a site on the known nucleotide sequence to hybridize therewith, $Y''_q$ represents a separation portion comprising at least two universal bases, $Z''_r$ represents a 3'-low $T_m$ specificity portion having a hybridizing nucleotide sequence substantially complementary to a site on the known nucleotide sequence to hybridize therewith, p, q and r represent the number of nucleotides, and X", Y", and Z" are deoxyribonucleotide or ribonucleotide; the $T_m$ of the 5'-high $T_m$ specificity portion is higher than that of the 3'-low $T_m$ specificity portion, the separation portion has the lowest $T_m$ in the three portions; the separation portion forms a non base-pairing bubble structure under conditions that the 5'-high $T_m$ specificity portion and the 3'-low $T_m$ specificity portion are annealed to the template nucleic acid, enabling the 5'-high $T_m$ specificity portion to separate from the 3'-low $T_m$ specificity portion in terms of annealing specificity to a template nucleic acid, whereby the annealing specificity of the primer is determined dually by the 5'-high $T_m$ specificity portion and the 3'-low $T_m$ specificity portion such that the overall annealing specificity of the primer is enhanced.

9. The method according to claim 1, wherein the universal base or non-discriminatory base analog residue is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy-beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4- nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-O-methoxyethyl inosine, 2'O-methoxyethyl nebularine, 2'-O-methoxyethyl 5-nitroindole, 2'-O-methoxyethyl 4-nitrobenzimidazole, 2'-O-methoxyethyl 3-nitropyrrole, and combinations thereof.

10. The method according to 9, wherein the universal base or non-discriminatory base analog residue is deoxyinosine, inosine, 1-(2'-deoxy-beta-D-ribofuranosyl)-3-nitropyrrole or 5-nitroindole.

11. The method according to claim 1, wherein the regulator portion in at least one DW-ACP comprises contiguous nucleotides having universal bases or non-discriminatory base analog residues.

12. The method according to claim 1, wherein p represents an integer of 10 to 60.

13. The method according to claim 1, wherein q or u is at least 3.

14. The method according to claim 1, wherein q or u represents an integer of 3 to 10.

15. The method according to claim 1, wherein r or v represents an integer of 2 to 5.

16. The method according to claim 1, wherein s or w represents an integer of 3 to 10.

17. The method according to claim 1, wherein S comprises at least 2 contiguous deoxyguanosine nucleotides.

18. The method according to claim 8, wherein the 5'-high $T_m$ specificity portion is longer than the 3'-low $T_m$ specificity portion.

19. The method according to claim 8, wherein the 3'-low $T_m$ specificity portion has a hybridizing nucleotide sequence perfectly complementary to the site on the known nucleotide sequence to hybridize therewith.

20. The method according to claim 8, wherein the 5'-high $T_m$ specificity portion is 15 to 40 nucleotides in length.

21. The method according to claim 8, wherein the 3'-low $T_m$ specificity portion is 3 to 15 nucleotides in length.

22. The method according to claim 8, wherein the 5'-high $T_m$ specificity portion is 15 to 25 nucleotides in length, the separation portion is 3 to 10 nucleotides in length, and the 3'-low $T_m$ specificity portion is 3 to 15 nucleotides in length.

23. The method according to claim 8, wherein the $T_m$ of the 5'-high $T_m$ specificity portion ranges from 40° C. to 80° C.

24. The method according to claim 8, wherein the $T_m$ of the 3'-low $T_m$ specificity portion ranges from 10° C. to 40° C.

25. The method according to claim 8, wherein the $T_m$ of the separation portion ranges from 3° C. to 15° C.

* * * * *